US010231910B2

(12) United States Patent
Lei et al.

(10) Patent No.: US 10,231,910 B2
(45) Date of Patent: Mar. 19, 2019

(54) ORAL CARE COMPOSITIONS HAVING IMPROVED FRESHNESS

(71) Applicant: The Procter & Gamble Company, Cincinnati, OH (US)

(72) Inventors: Zhong Lei, Beijing (CN); Jun Pei, Beijing (CN); Ross Strand, Beijing (CN); Hongmei Yang, Beijing (CN); Yan Zhang, Beijing (CN)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 14/682,146

(22) Filed: Apr. 9, 2015

(65) Prior Publication Data

US 2015/0328091 A1 Nov. 19, 2015

(30) Foreign Application Priority Data

May 15, 2014 (CN) ................ 2014/077538

(51) Int. Cl.
| | |
|---|---|
| *A61K 8/19* | (2006.01) |
| *A61K 8/24* | (2006.01) |
| *A61Q 11/00* | (2006.01) |
| *A61K 8/34* | (2006.01) |
| *A61K 8/35* | (2006.01) |
| *A61K 8/46* | (2006.01) |
| *A61K 8/73* | (2006.01) |
| *A61K 8/25* | (2006.01) |

(52) U.S. Cl.
CPC ............ *A61K 8/19* (2013.01); *A61K 8/24* (2013.01); *A61K 8/25* (2013.01); *A61K 8/34* (2013.01); *A61K 8/35* (2013.01); *A61K 8/463* (2013.01); *A61K 8/73* (2013.01); *A61K 8/731* (2013.01); *A61Q 11/00* (2013.01); *A61K 2800/28* (2013.01); *A61K 2800/48* (2013.01); *A61K 2800/592* (2013.01); *A61K 2800/594* (2013.01); *A61K 2800/92* (2013.01)

(58) Field of Classification Search
CPC ... A61K 8/25; A61K 8/19; A61K 8/34; A61K 8/35; A61K 8/24; A61K 8/731; A61K 8/463; A61K 8/73; A61K 2800/594; A61K 2800/28; A61K 2800/92; A61K 2800/48; A61K 2800/592; A61Q 11/00
See application file for complete search history.

(56) References Cited

U.S. PATENT DOCUMENTS

| | | | |
|---|---|---|---|
| 3,119,743 A | 1/1964 | Yngve | |
| 4,046,872 A | 9/1977 | Mitchell et al. | |
| 4,283,385 A | 8/1981 | Dhabhar et al. | |
| 4,469,673 A | 9/1984 | Iioka et al. | |
| 4,565,691 A | 1/1986 | Jackson | |
| 4,574,081 A | 3/1986 | Shymon | |
| 4,678,662 A | 7/1987 | Chan | |
| 4,701,319 A | 10/1987 | Woo | |
| 4,828,849 A | 5/1989 | Lynch et al. | |
| 5,626,837 A | 5/1997 | Shimada et al. | |
| 5,939,052 A | 8/1999 | White, Jr. et al. | |
| 6,106,811 A | 8/2000 | Gibbs | |
| 6,159,446 A | 12/2000 | Randive et al. | |
| 6,696,045 B2 | 2/2004 | Yue et al. | |
| 6,723,304 B2 * | 4/2004 | Stier | A61Q 11/00 424/48 |
| 7,648,363 B2 | 1/2010 | Oniki et al. | |
| 8,007,771 B2 | 8/2011 | Ramji et al. | |
| 2002/0001569 A1 | 1/2002 | Dromard et al. | |
| 2003/0003061 A1 | 1/2003 | Yue et al. | |
| 2003/0072721 A1 | 4/2003 | Riley et al. | |
| 2003/0095931 A1 | 5/2003 | Stier | |
| 2003/0202946 A1 * | 10/2003 | Hanada | A61K 8/02 424/49 |
| 2004/0120902 A1 | 6/2004 | Wernett et al. | |
| 2004/0131560 A1 | 7/2004 | Corcoran et al. | |
| 2006/0134020 A1 | 6/2006 | Robinson et al. | |
| 2006/0159631 A1 | 7/2006 | Buch et al. | |
| 2007/0231278 A1 | 10/2007 | Lee et al. | |
| 2008/0008729 A1 | 1/2008 | Swaine et al. | |
| 2008/0230298 A1 | 9/2008 | Buch et al. | |
| 2009/0136432 A1 | 5/2009 | Strand et al. | |

(Continued)

FOREIGN PATENT DOCUMENTS

| | | |
|---|---|---|
| CN | 1633967 | 7/2005 |
| CN | 101690699 | 4/2010 |

(Continued)

OTHER PUBLICATIONS

Pearce, et al. "The Effect of pH, Temperature and Plaque Thickness on the Hydrolysis of Monofluorophosphate in Experimental Dental Plaque", Caries Research, vol. 37, pp. 178-184, Feb. 1, 2003.
PCT/CN2014/077538 International Search Report dated Feb. 17, 2015.
All Office Actions, U.S. Pat. No. 9,687,427.
All Office Actions, U.S. Appl. No. 14/633,389.
All Office Actions, U.S. Pat. No. 9,498,416.
All Office Actions, U.S. Appl. No. 15/294,855.
All Office Actions, U.S. Appl. No. 14/634,969.
All Office Actions, U.S. Appl. No. 14/635,234.
All Office Actions, U.S. Appl. No. 14/700,182.
All Office Actions, U.S. Appl. No. 14/830,815.
All Office Actions, U.S. Appl. No. 14/634,993.

(Continued)

*Primary Examiner* — Lezah Roberts
(74) *Attorney, Agent, or Firm* — Parker D. McCrary; Alexandra S. Anoff; James E. Oehlenschlager (57) ABSTRACT

An oral care composition comprising 20% to 75% of water by weight of the composition; 25% to 60% of a calcium-containing abrasive by weight of the composition; 0.001% to 5% of a flavorant by weight of the composition; and a rheology profile characterized by at least one of the following parameters: 10*K (Pa·s) value from 100 to 3,000; (−10000*)n (rate index) value from −5000 to −1300; 10*Yield Stress value from 100 to 3,500; Average G' value from 100 to 2000; or Average G" value 100 to 1000.

7 Claims, 2 Drawing Sheets

(56) References Cited

U.S. PATENT DOCUMENTS

| | | |
|---|---|---|
| 2009/0136584 A1 | 5/2009 | Hosoya et al. |
| 2009/0269287 A1 | 10/2009 | Berta |
| 2010/0086498 A1 | 4/2010 | Haught et al. |
| 2010/0135921 A1* | 6/2010 | Hughes .................. A61K 8/25 424/49 |
| 2010/0278991 A1 | 11/2010 | Haught et al. |
| 2012/0020897 A1 | 1/2012 | Campbell et al. |
| 2012/0189561 A1 | 7/2012 | Randive et al. |
| 2013/0064779 A1 | 3/2013 | Yamane et al. |
| 2013/0084254 A1 | 4/2013 | Alonso et al. |
| 2013/0251647 A1 | 9/2013 | Subkowski et al. |
| 2013/0280182 A1 | 10/2013 | Burgess et al. |
| 2013/0344120 A1 | 12/2013 | Scott et al. |
| 2014/0314690 A1 | 10/2014 | Fisher et al. |
| 2017/0014321 A1 | 1/2017 | D'Ambrogio et al. |
| 2017/0014322 A1 | 1/2017 | D'Ambrogio et al. |

FOREIGN PATENT DOCUMENTS

| | | |
|---|---|---|
| FR | 2419726 | 10/1979 |
| GB | 708232 * | 5/1954 |
| JP | H05194166 A | 8/1993 |
| JP | H1112143 | 1/1999 |
| JP | 2003063938 A | 3/2003 |
| JP | 2008544869 A | 12/2008 |
| KR | 2002/0054045 A | 7/2002 |
| KR | 2012/0042399 A | 5/2012 |
| WO | WO 2007/122146 A1 | 11/2007 |
| WO | WO2013034421 | 3/2013 |
| WO | WO2013094312 | 6/2013 |

OTHER PUBLICATIONS

All Office Actions, U.S. Appl. No. 14/830,831.
All Office Actions, U.S. Appl. No. 14/634,949.
All Office Actions, U.S. Pat. No. 9,364,419.
All Office Actions, U.S. Appl. No. 15/150,486.
All Office Actions, U.S. Appl. No. 14/682,141.
All Office Actions, U.S. Appl. No. 14/682,146.
All Office Actions, U.S. Appl. No. 14/700,196.
All Office Actions, U.S. Appl. No. 14/830,839.
All Office Actions, U.S. Appl. No. 14/736,352.
PCT/CN2014/077538 Supplementary International Search Report dated Aug. 10, 2016.

* cited by examiner

ORAL CARE COMPOSITIONS HAVING IMPROVED FRESHNESS

CROSS REFERENCE TO RELATED APPLICATION

This Application claims the benefit of Application No. CN2014/077538, filed May 15, 2014.

FIELD OF THE INVENTION

The present invention relates to oral care compositions having freshness benefits.

BACKGROUND OF THE INVENTION

Oral care compositions are well known for dental and oral hygiene care. High water (e.g., >45 wt %) and high carbonate (e.g., >25 wt %) formulation chassis are a cost effective for many markets and consumers. Oral care compositions often contain flavorant composition to provide a desirable experience for the user as well as impart fresh breath benefits, for example, after brushing with a dentifrice. Many dentists recommend brushing teeth for at least two minutes. Accordingly, it is desirable to provide the user with the maximum flavor release as soon as possible so the user may best experience the flavor for the maximized duration during the brushing episode (or other oral treatment regimen).

SUMMARY OF THE INVENTION

The present invention is based, in part, on the surprising observation that rheology is an important parameter in increasing the rate of flavor display during a user's tooth brushing episode. Accordingly, one aspect of the invention provides an oral care composition comprising: (a) 20% to 75%, preferably 50% to 60%, of water by weight of the composition; (b) 25% to 60%, preferably 27% to 47%, of a calcium-containing abrasive by weight of the composition, preferably wherein the calcium-containing abrasive is calcium carbonate; (c) 0.001% to 5% of a flavorant composition; and (d) a rheology profile characterized by at least one parameter of the following parameters, preferably at least any two of the following parameters, alternatively at least any three of the following parameters, alternatively at least any four of the following parameters, alternatively five of the following parameters: (i) 10*K (Pa·s) value less than 3,000, preferably less than 2,750, preferably less than 2,500, alternatively from 100 to 3,000, alternatively from 1,000 to 2,500, alternatively combinations thereof; (ii) (−10000*)n (rate index) value less than −1500, preferably less than −2,000, more preferably less than −2,500, alternatively from −5000 to −1300, alternatively from −4000 to −1,400; alternatively combinations thereof; (iii) 10*Yield Stress value less than 4000, preferably less than 3,500, more preferably less than 3,000, yet still more preferable less than 2,750, alternatively from 500 to 3,750, alternatively from 100 to 3,500, alternatively combinations thereof; (iv) Average G' value is less than 4,250, preferably less than 4,000, more preferably less than 3,000, yet more preferable less than 2,000, yet still more preferably less than 1,500, alternatively from 100 to 2000, alternatively from 500 to 1,500, alternatively combinations thereof; and (v) Average G" value less than 1,500, preferably less than 1000, more preferably less than 750, yet more preferably less than 500, alternatively from 50 to 1500, alternatively from 100 to 1000, alternatively from 10 to 500, alternatively combinations thereof.

Another surprising observation is that surfactant also plays a role in the rate of flavor display, and that more efficient use of surfactant may be used by including a calcium chelating agent in the formulation (e.g., tetrasodium pyrophosphate (TSPP)). Therefore, a lower amount of surfactant may be used and yet still achieve desirable flavor release rate when in the presence of a calcium chelating agent. Without wishing to be bound by theory, a chelating agent such as TSPP can minimize the occurrence of aggregation that may form between calcium ions and surfactant (such as sodium lauryl sulfate (SLS)). In one embodiment of the invention, the oral care composition comprises 0.01% to 1.35%, preferably from 0.1% to 1%, more preferably from 0.1% to less than 1.0% of a pyrophosphate ion source by weight of the composition, preferably wherein the pyrophosphate ion source is a pyrophosphate salt, more preferably wherein the pyrophosphate is tetrasodium pyrophosphate.

One advantage of the present invention is an increased rate of providing maximum freshness to users. One aspect of the invention provides an oral care composition comprising: (a) 20% to 75%, preferably 50% to 60%, of water by weight of the composition; (b) 25% to 60%, preferably 27% to 47%, of a calcium-containing abrasive by weight of the composition, preferably wherein the calcium-containing abrasive is calcium carbonate; (c) 0.001% to 5% of a flavorant composition, wherein the flavorant composition comprises a menthol; and wherein the composition has an Flavor Blooming Index (FBI) of menthol of at least one of the following, preferably at least two of the following, more preferably at least three of the following: (i) FBI is greater than 250 at 40 seconds, preferably greater than 300, more preferably greater than 350, alternatively greater than 400, alternatively from 250 to 1,000, alternatively from 300 to 800; (ii) FBI is greater than 290 at 60 seconds, preferably greater than 300, more preferably greater than 350, alternatively greater than 375, alternatively greater than 400, alternatively from 300 to 1000, alternatively from 350 to 800; (iii) FBI is greater than 330 at 120 seconds, preferably greater than 350, more preferably greater than 375, yet more preferably greater than 400, alternatively from 340 to 1,000, alternatively from 250 to 800.

Another aspect of the invention provides an oral care composition comprising: (a) 20% to 75%, preferably 50% to 60%, of water by weight of the composition; (b) 25% to 60%, preferably 27% to 47%, of a calcium-containing abrasive by weight of the composition, preferably wherein the calcium-containing abrasive is calcium carbonate; (c) 0.001% to 5% of a flavorant composition, wherein the flavorant composition comprises a menthone; and wherein the composition has a Flavor Blooming Index (FBI) of menthone of at least one of the following, preferably at least two of the following, more preferably at least three of the following: (i) FBI is greater than 950 at 40 seconds, preferably greater than 1,000, more preferably greater than 1,100, yet more preferably greater than 1,200, yet still more preferably greater than 1,300, alternatively greater than 1,400, alternatively from 1,000 to 2,000, alternatively from 1,100 to 3,000; (ii) FBI is greater than 950 at 60 seconds, preferably greater than 1,000, more preferably greater than 1,100, yet more preferably greater than 1,200, yet still more preferably greater than 1,300, alternatively greater than 1,400, alternatively from 1,000 to 2,000, alternatively from 1,100 to 3,000; and (iii) FBI is greater than 1,100 at 120 seconds, preferably greater than 1,200, more preferably greater than 1,300, alternatively greater than 1,400, alternatively from 1,100 to 2,000, alternatively from 1,200 to 3,000.

Another advantage of the present invention is to provide a desirable rate of freshness while minimizing the level of surfactant. By minimizing the level of surfactant, cost savings achieved as well as mitigating possible effects to users with higher levels of surfactant is used. In one embodiment of the invention, the oral care composition comprises from 0.1% to 12% of a surfactant by weight of the composition, preferably from 0.1% to 9%, more preferably 0.2% to 4% of the surfactant, more preferably wherein the surfactant is an anionic surfactant, yet more preferably wherein the anionic surfactant is sodium lauryl sulfate (SLS).

One aspect of the invention provides an oral care composition comprising: (a) 20% to 75%, preferably 50% to 60%, of water by weight of the composition; (b) 25% to 60%, preferably 27% to 47%, of a calcium-containing abrasive by weight of the composition, preferably wherein the calcium-containing abrasive is calcium carbonate; (c) 0.001% to 5% of a flavorant composition; (d) 0.01% to 1.35%, preferably from 0.1% to 1%, more preferably from 0.1% to less than 1.0% of a pyrophosphate ion source by weight of the composition, preferably wherein the pyrophosphate ion source is a pyrophosphate salt, more preferably wherein the pyrophosphate is tetrasodium pyrophosphate; (e) 0.01% to less than 1.4%, preferably from 0.1% to 1.3%, more preferably from 0.5% to 1.3% of a carrageenan by weight of the composition; (f) greater than 0.4% to 2%, preferably from 0.5% to 1.8%, more preferably from 0.6% to 1.8% of a carboxymethyl cellulose by weight of the composition; (g) 0.5% to 5%, preferably 1% to 4%, of a thickening silica by weight of the composition; (h) 0.1% to 12%, preferably from 0.2% to 4%, of a surfactant by weight of the composition, more preferably wherein the surfactant is an anionic surfactant, yet more preferably wherein the anionic surfactant is sodium lauryl sulfate (SLS); and (i) pH is greater than 7.8, preferably greater than 8.3, more preferably the pH from 8.5 to 12.

Yet another aspect of the invention provides a method of treating tooth enamel comprising the step of brushing teeth with the dentifrice compositions herein described.

While the specification concludes with claims that particularly point out and distinctly claim the invention, it is believed the present invention will be better understood from the following description.

DETAILED DESCRIPTION OF THE INVENTION

Definitions

The term "orally acceptable carrier" as used herein means a suitable vehicle or ingredient, which can be used to form and/or apply the present compositions to the oral cavity in a safe and effective manner.

The term "comprising" as used herein means that steps and ingredients other than those specifically mentioned can be added. This term encompasses the terms "consisting of" and "consisting essentially of." The compositions of the present invention can comprise, consist of, and consist essentially of the essential elements and limitations of the invention described herein, as well as any of the additional or optional ingredients, components, steps, or limitations described herein.

The term "effective amount" as used herein means an amount of a compound or composition sufficient to induce a positive benefit, an oral health benefit, and/or an amount low enough to avoid serious side effects, i.e., to provide a reasonable benefit to risk ratio, within the sound judgment of a skilled artisan. In one embodiment, "effective amount" means at least 0.01% of the material, by weight of the composition, alternatively at least 0.1%.

The term "oral composition" as used herein means a product that in the ordinary course of usage is retained in the oral cavity for a time sufficient to contact some or all of the dental surfaces and/or oral tissues for purposes of oral activity. In one embodiment, the composition is an "oral care composition" meaning that the composition provides a benefit when used in the oral cavity. The oral composition of the present invention may be in various forms including toothpaste, dentifrice, tooth gel, tooth powders, tablets, rinse, sub gingival gel, foam, mousse, chewing gum, lipstick, sponge, floss, prophy paste, petrolatum gel, or denture product. In one embodiment, the oral composition is in the form of a paste or gel. In another embodiment, the oral composition is in the form of a dentifrice. The oral composition may also be incorporated onto strips or films for directing application or attachment to oral surfaces, or incorporated into floss.

The term "dentifrice" as used herein means paste, gel, powder, tablets, or liquid formulations, unless otherwise specified, that are used to clean the surfaces of the oral cavity. The term "teeth" as used herein refers to natural teeth as well as artificial teeth or dental prosthesis.

All percentages, parts and ratios are based upon the total weight of the compositions of the present invention, unless otherwise specified. All such weights as they pertain to listed ingredients are based on the active level and, therefore do not include solvents or by-products that may be included in commercially available materials, unless otherwise specified. The term "weight percent" may be denoted as "wt %" herein. All molecular weights as used herein are weight average molecular weights expressed as grams/mole, unless otherwise specified.

As used herein, the articles including "a" and "an" when used in a claim, are understood to mean one or more of what is claimed or described.

As used herein, the terms "comprise", "comprises", "comprising", "include", "includes", "including", "contain", "contains", and "containing" are meant to be non-limiting, i.e., other steps and other sections which do not affect the end of result can be added. The above terms encompass the terms "consisting of" and "consisting essentially of".

As used herein, the words "preferred", "preferably" and variants refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

Water

The compositions of the present invention comprise herein from 20% to 75%, by weight of the composition of total water. In one embodiment, the composition includes from 40% to 70%, alternatively from 45% to 65%, alternatively from 40% to 60%, alternatively from 50% to 70%, alternatively from 50% to 60%, alternatively from 45% to 55%, alternatively from 55% to 65%, alternatively from 50% to 60%, alternatively about 55%, alternatively combinations thereof, of water by weight of the composition. The water may be added to the formulation and/or may come into the composition from the inclusion of other ingredients. Preferably the water is USP water.

Calcium-Containing Abrasive

The compositions of the present invention comprise from 20% to 60% by weight of a calcium-containing abrasive, wherein the calcium-containing abrasive is selected from the group consisting of calcium carbonate, dicalcium phosphate, tricalcium phosphate, calcium orthophosphate, calcium metaphosphate, calcium polyphosphate, calcium oxyapatite, sodium carbonate, and combinations thereof. In a preferred embodiment, the composition comprises from 25% to 60%, more preferably from 25% to 50%, even more preferably from 25% to 40%, yet even more preferably from 26% to 39%, alternatively from 27% to 47%, alternatively from 27% to 37%, alternatively from 30% to 35%, alternatively from 30% to 34%, alternatively combinations thereof, of a calcium-containing abrasive by weight of the composition.

In one embodiment, the calcium-containing abrasive is calcium carbonate. In a preferred embodiment, the calcium-containing abrasive is selected from the group consisting of fine ground natural chalk, ground calcium carbonate, precipitated calcium carbonate, and combinations thereof.

Fine ground natural chalk (FGNC) is one of the more preferred calcium-containing abrasives useful in the present invention. It is obtained from limestone or marble. FGNC may also be modified chemically or physically by coating during milling or after milling by heat treatment. Typical coating materials include magnesium stearate or oleate. The morphology of FGNC may also be modified during the milling process by using different milling techniques, for example, ball milling, air-classifier milling or spiral jet milling. One example of natural chalk is described in WO 03/030850 having a medium particle size of 1 to 15 μm and a BET surface area of 0.5 to 3 $m^2/g$. The natural calcium carbonate may have a particle size of 325 to 800 mesh, alternatively a mesh selected from 325, 400 600, 800, or combinations thereof; alternatively the particle is s from 0.1 to 30 microns, or from 0.1 to 20 microns, or from 5 to 20 microns In one embodiment, the composition of the present invention is free or substantially free of silicate.

PEG

The compositions of the present invention may comprise polyethylene glycol (PEG), of various weight percentages of the composition as well as various ranges of average molecular weights. In one aspect of the invention, the compositions have from 0.1% to 15%, preferably from 0.2% to 12%, more preferably from 0.3% to 10%, yet more preferably from 0.5% to 7%, alternatively from 1% to 5%, alternatively from 1% to 4%, alternatively from 1% to 2%, alternatively from 2% to 3%, alternatively from 4% to 5%, or combinations thereof, of PEG by weight of the composition. In another aspect of the invention, the PEG is one having a range of average molecular weight from 100 Daltons to 1600 Daltons, preferably from 200 to 1000, alternatively from 400 to 800, alternatively from 500 to 700 Daltons, alternatively combinations thereof. PEG is a water soluble linear polymer formed by the addition reaction of ethylene oxide to an ethylene glycol equivalent having the general formula: $H—(OCH_2CH_2)_n—OH$. One supplier of PEG is Dow Chemical Company under the brandname of CARBOWAX™.

Sweetener

The oral care compositions herein may include a sweetening agent. These include sweeteners such as saccharin, dextrose, sucrose, lactose, maltose, levulose, aspartame, sodium cyclamate, D-tryptophan, dihydrochalcones, acesulfame, sucralose, neotame, and mixtures thereof. Sweetening agents are generally used in oral compositions at levels of from 0.005% to 5%, by weight of the composition, alternatively 0.01% to 1%, alternatively from 0.1% to 0.5%, alternatively combinations thereof.

Fluoride Ion Source

The composition may include an effective amount of an anti-caries agent. In one embodiment, the anti-caries agent is a fluoride ion source. The fluoride ion may be present in an amount sufficient to give a fluoride ion concentration in the composition at 25° C., and/or in one embodiment can be used at levels of from about 0.0025% to about 5% by weight of the composition, alternatively from about 0.005% to about 2.0% by weight of the composition, to provide anti-caries effectiveness. Examples of suitable fluoride ion-yielding materials are disclosed in U.S. Pat. Nos. 3,535,421, and 3,678,154. Representative fluoride ion sources include: stannous fluoride, sodium fluoride, potassium fluoride, amine fluoride, sodium monofluorophosphate, and zinc fluoride. In one embodiment the oral care composition contains a fluoride source selected from stannous fluoride, sodium fluoride, and mixtures thereof. In one embodiment, the fluoride ion source is sodium monofluorophosphate, and wherein the composition comprises 0.0025% to 2% of the sodium monofluorophosphate by weight of the composition, alternatively from 0.5% to 1.5%, alternatively from 0.6% to 1.7%, alternatively combinations thereof. In another embodiment, the composition comprises from 0.0025% to 2% of a fluoride ion source by weight of the composition.

pH

The pH of the oral composition may be greater than pH 7.8, or greater than pH 8.3, or a pH from 8 to 13, or a pH from 8.3 to 13, more preferably a pH from 9 to 12, alternatively greater than pH 8, alternatively greater than pH 9, alternatively from a pH from 9 to 11, alternatively a pH from 9 to 10, or combinations thereof.

A method for assessing pH of dentifrice is described. pH is measured by a pH Meter with Automatic Temperature Compensating (ATC) probe. The pH Meter is capable of reading to 0.001 pH unit. The pH electrode may be selected from one of the following (i) Orion Ross Sure-Flow combination: Glass body-VWR #34104-834/Orion #8172BN or VWR#10010-772/Orion #8172BNWP; Epoxy body-VWR #34104-830/Orion #8165BN or VWR#10010-770/Orion #8165BNWP; Semi-micro, epoxy body-VWR #34104-837/Orion #8175BN or VWR#10010-774/Orion #3175BNWP; or (ii) Orion PerpHect combination: VWR #34104-843/Orion #8203BN semi-micro, glass body; or (iii) suitable equivalent. The automatic temperature compensating probe is Fisher Scientific, Cat #13-620-16.

A 25% by weight slurry of dentifrice is prepared with deionized water, and thereafter is centrifuged for 10 minutes at 15000 rotations-per-minute using a SORVALL RC 28S centrifuge and SS-34 rotor (or equivalent gravitational force, at 24149 g force). The pH is assessed in supernatant after one minute or the taking reading is stabilized. After each pH assessment, the electrode is washed with deionized water. Any excess water is wiped with a laboratory grade tissue. When not in issue, the electrode is kept immersed in a pH 7 buffer solution or an appropriate electrode storage solution.

pH Modifying Agent

The oral care compositions herein may include an effective amount of a pH modifying agent, alternatively wherein the pH modifying agent is a pH buffering agent. pH modifying agents, as used herein, refer to agents that can be used to adjust the pH of the dentifrice compositions to the above-identified pH range. pH modifying agents may include alkali metal hydroxides, ammonium hydroxide, organic ammonium compounds, carbonates, sesquicarbonates, borates, silicates, phosphates, imidazole, and mixtures thereof. Specific pH agents include monosodium phosphate (monobasic sodium phosphate), trisodium phosphate (sodium phosphate tribasic dodecahydrate or TSP), sodium benzoate, benzoic acid, sodium hydroxide, potassium hydroxide, alkali metal carbonate salts, sodium carbonate, imidazole, pyrophosphate salts, sodium gluconate, lactic acid, sodium lactate, citric acid, sodium citrate, phosphoric acid. In one embodiment, 0.01% to 3%, preferably from 0.1% to 1% of TSP by weight of the composition, and 0.001% to 2%, preferably from 0.01% to 0.3% of monosodium phosphate by weight of the composition is used. Without wishing to be bound by theory, TSP and monosodium phosphate may also have calcium ion chelating activity and therefore provide some monofluorophosphate stabilization (in those formulations containing monoflurophospahte).

Anti-Calculus Agent

The oral care compositions may include an effective amount of an anti-calculus agent, which in one embodiment may be present from about 0.05% to about 50%, by weight of the oral care composition, alternatively from about 0.05% to about 25%, alternatively from about 0.1% to about 15%. Non-limiting examples include those described in US 2011/0104081 A1 at paragraph 64, and those described in US 2012/0014883 A1 at paragraphs 63 to 68, as well as the references cited therein. One example is a pyrophosphate salt as a source of pyrophosphate ion. In one embodiment, the composition comprises tetrasodium pyrophosphate (TSPP) or disodium pyrophosphate or combinations thereof, preferably 0.01% to 2%, more preferably from 0.1% to 1% of the pyrophosphate salt by weight of the composition. Without wishing to be bound by theory, TSPP may provide not only calcium chelating thereby mitigating plaque formation, but also may also provide the additional benefit of monofluorophosphate stabilization (in those formulations containing monofluorophosphate).

Surfactant

The compositions herein may include a surfactant. The surfactant may be selected from anionic, nonionic, amphoteric, zwitterionic, cationic surfactants, or mixtures thereof. The oral care composition may include a surfactant at a level of from about 0.1% to about 10%, from about 0.025% to about 9%, from about 0.05% to about 5%, from about 0.1% to about 2.5%, from about 0.5% to about 2%, or from about 0.1% to about 1% by weight of the total composition. Non-limiting examples of anionic surfactants may include those described at US 2012/0082630 A1 at paragraphs 32, 33, 34, and 35. Non-limiting examples of zwitterionic or amphoteric surfactants may include those described at US 2012/0082630 A1 at paragraph 36; cationic surfactants may include those described at paragraph 37 of the reference; and nonionic surfactants may include those described at paragraph 38 of the reference. In one embodiment the composition comprises 0.1% to 5%, preferably 0.1% to 3%, alternatively from 0.3% to 3%, alternatively from 1.2% to 2.4%, alternatively from 1.2% to 1.8%, alternatively from 1.5% to 1.8%, alternatively combinations thereof, of the anionic surfactant sodium lauryl sulfate (SLS) by weight of the composition.

Thickening Agent

The oral care compositions herein may include one or more thickening agents. A thickening agent may be used in an amount from about 0.01% to about 15%, or from about 0.1% to about 10%, or from about 0.1% to about 5%, by weight of the composition. Non-limiting examples may include those described in US 2008/0081023 A1 at paragraphs 134 to 137, and the references cited therein.

In embodiment, the composition comprises a linear sulfated polysaccharide as a thickening agent. Carrageenans or carrageenins are one example of a linear sulfated polysaccharide. Generally, carrageenans can vary based upon the degree of sulfation that include: Kappa-carrageenan, Iota-carrageenan, and Lambda-carrageenan. Combinations of carrageenans can be used. In one embodiment, the composition contains from 0.1% to 3% of a linear sulfated polysaccharides by weight of the composition, preferably from 0.5% to 2%, alternatively from 0.6% to 1.8%, alternatively combinations thereof. In one embodiment, Iota-carrageenan is used.

In one embodiment, the composition comprises a silica agent, preferably a thickening silica obtained from sodium silicate solution by destabilizing with acid as to yield very fine particles. One commercially available example is ZEODENT® branded silica from Huber Engineered Materials (e.g., ZEODENT® 103, 124, 113 115, 163, 165, 167). In one embodiment, the composition comprising from 0.5% to 5% by weight of the composition of a silica agent, preferably from 1% to 4%, alternatively from 1.5% to 3.5%, alternatively from 2% to 3%, alternatively from 2% to 5%, alternatively from 1% to 3%, alternatively combinations thereof.

In one embodiment, the composition comprises a carboxymethyl cellulose ("CMC"). CMC is prepared from cellulose by treatment with alkali and monochloro-acetic acid or its sodium salt. Different varieties are commercially characterized by viscosity. One commercially available example is Aqualon™ branded CMC from Ashland Special Ingredients (e.g., Aqualon™ 7H3SF; Aqualon™ 9M3SF Aqualon™ TM9A; Aqualon™ TM12A). In one embodiment, the composition contains from 0.1% to 3% of a CMC by weight of the composition, preferably from 0.5% to 2%, alternatively from 0.6% to 1.8%, alternatively combinations thereof.

In yet another embodiment, the thickener agents may comprise liner sulfated polysaccharide (e.g., carrageenans), CMC, and preferably also a thickening silica for purposes of cost savings while achieving the right balancing of viscosity and elasticity. In one embodiment, the composition comprises a thickener comprising: (a) 0.01% to less than 1.4%, preferably from 0.1% to 1.3%, more preferably from 0.5% to 1.3% of a carrageenan by weight of the oral care composition; and (d) greater than 0.4% to 2%, preferably from 0.5% to 1.8%, more preferably from 0.6% to 1.8% of a carboxymethyl cellulose (CMC) by weight of the oral care composition. In yet another embodiment, the aforementioned thickener further comprises 0.5% to 5%, preferably 1% to 4%, of a thickening silica by weight of the oral care composition.

Low or Free Humectants

The compositions herein may be substantially free or free of humectants, alternatively contain low levels of humectants. The term "humectant," for the present invention, includes edible polyhydric alcohols such as glycerin, sorbitol, xylitol, butylene glycol, propylene glycol, and combinations thereof. In one embodiment, the humectant is selected from sorbitol, glycerin, and combinations thereof. In yet another embodiment, the humectant is sorbitol. In one embodiment, the composition comprises from 0% to less than 20% of humectants by weight of the composition, preferably from 0% to 10%, alternatively from 0% to 5%, alternatively from 0% to 3%, alternatively from 0% to 2%, alternatively from 0% to 1%, alternatively less than 20%, or less than 19%, 18%, 15%, 12%, 8%, 7%, 6%, 4%, 3%, 2%, 1%, or less than 0.5%; or greater than 1%, or greater than 2%, 5%, 10%, or 15%; or combinations thereof, by weight of the composition. In yet another embodiment, the composition contains less than 20% of sorbitol by weight of the composition.

In an alternative embodiment, the compositions of the present invention comprise a humectant, preferably from 1% to 15% by weight of the composition.

Colorant

The oral care compositions herein may include a colorant. Titanium dioxide is one example of a colorant. Titanium dioxide is a white powder which adds opacity to the compositions. Titanium dioxide generally can comprise from about 0.25% to about 5%, by weight of the composition.

Flavorant

The compositions herein may include from about 0.001% to about 5%, alternatively from about 0.01% to about 4%, alternatively from about 0.1% to about 3%, alternatively from about 0.5% to about 2%, alternatively 1% to 1.5%, alternatively 0.5% to 1%, alternatively combinations thereof, of a flavorant composition by weight of the composition. The term flavorant composition is used in the broadest sense to include flavor ingredients, or sensates, or sensate agents, or combinations thereof. Flavor ingredients may include those described in US 2012/0082630 A1 at paragraph 39; and sensates and sensate ingredients may include those described at paragraphs 40-45, incorporated herein by reference. Excluded from the definition of flavorant composition is "sweetener" (as described above).

Examples of flavor compositions or flavor ingredients include: mint oils, wintergreen, clove bud oil, cassia, sage, parsley oil, marjoram, lemon, orange, propenyl guaethol, heliotropine, 4-cis-heptenal, diacetyl, methyl-p-tert-butyl phenyl acetate, methyl salicylate, ethyl salicylate, 1-menthyl acetate, oxanone, a-irisone, methyl cinnamate, ethyl cinnamate, butyl cinnamate, ethyl butyrate, ethyl acetate, methyl anthranilate, iso-amyl acetate, iso-amyl butyrate, allyl caproate, eugenol, eucalyptol, thymol, cinnamic alcohol, octanol, octanal, decanol, decanal, phenylethyl alcohol, benzyl alcohol, a-terpineol, linalool, limonene, citral, neral, geranial, geraniol nerol, maltol, ethyl maltol, anethole, dihydroanethole, carvone, menthone, beta-damascenone, ionone, gamma-decalactone, gamma-nonalactone, y-undecalactone, or combinations thereof. Generally suitable flavor ingredients are chemicals with structural features and functional groups that are less prone to redox reactions. These include derivatives of flavor ingredients that are saturated or contain stable aromatic rings or ester groups.

Sensates such as cooling, warming, and tingling agents are useful to deliver signals to the consumer. The most well-known cooling agent is menthol, particularly 1-menthol, which is found naturally in peppermint oil. Among synthetic cooling agents, many are derivatives of or are structurally related to menthol, i.e., containing the cyclohexane moiety, and derivatized with functional groups including carboxamide, ketal, ester, ether and alcohol. Examples include the p-menthanecarboxamide compounds such as N-ethyl-p-menthan-3-carboxamide or N-(4-cyanomethylphenyl)-p-menthanecarboxamide (EVERCOOL 180). An example of a synthetic carboxamide cooling agent that is structurally unrelated to menthol is N,2,3-trimethyl-2-isopropylbutanamide. Additional exemplary synthetic cooling agents include alcohol derivatives such as 3-1-menthoxy-propane-1,2-diol, isopulegol, p-menthane-3,8-diol; menthone glycerol acetal; menthyl esters such as menthyl acetate, menthyl acetoacetate, menthyl lactate, and monomenthyl succinate.

Additional agents that are structurally unrelated to menthol but have been reported to have a similar physiological cooling effect include alpha-keto enamine derivatives described in U.S. Pat. No. 6,592,884, including 3-methyl-2-(1-pyrrolidinyl)-2-cyclopenten-1-one (3-MPC), 5-methyl-2-(1-pyrrolidinyl)-2-cyclopenten-1-one (5-MPC); 2,5-dimethyl-4-(1-pyrrolidinyl)-3(2H)-furanone (DMPF); icilin (also known as AG-3-5, chemical name 142-hydroxyphenyl]-4-[2-nitrophenyl]-1,2,3,6-tetrahydropyrimidine-2-one).

Some examples of warming agents include ethanol; nicotinate esters, such as benzyl nicotinate; polyhydric alcohols; nonanoyl vanillyl amide; nonanoic acid vanillyl ether; vanillyl alcohol alkyl ether derivatives such as vanillyl ethyl ether, vanillyl butyl ether, vanillyl pentyl ether, and vanillyl hexyl ether; isovanillyl alcohol alkyl ethers; ethylvanillyl alcohol alkyl ethers; veratryl alcohol derivatives; substituted benzyl alcohol derivatives; substituted benzyl alcohol alkyl ethers; vanillin propylene glycol acetal; ethylvanillin propylene glycol acetal; ginger extract; ginger oil; gingerol; zingerone; or combinations thereof.

Examples of some tingling agents include capsaicin, homocapsaicin, jambu oleoresin, zanthoxylum peperitum, saanshool-I, saanshool II, sanshoamide, piperine, piperidine, spilanthol, 4-(1-methoxymethyl)-2-phenyl-1,3-dioxolane, or combinations thereof.

One non-limiting example of a flavorant composition is "Flavor A." Flavor A is a flavorant composition comprising the following components and weight percentages relative to the flavorant composition at detailed in Table 1 below.

TABLE 1

| Flavor Ingredient | Chemical name | Weight Percent |
|---|---|---|
| trans-Anethole | 1-Methoxy-4-((E)-1-propenyl)-benzene | 11% |
| l-Menthone | (2S,5R)-5-methyl-2-propan-2-ylcyclohexan-1-one | 11.5% |
| Menthone | 5-methyl-2-propan-2-ylcyclohexan-1-one | 5.6% |
| L-Menthol | (1R,2S,5R)-5-methyl-2-propan-2-ylcyclohexan | 51% |
| (+)-Neomenthol | (1S,2S,5R)-5-methyl-2-propan-2-ylcyclohexan-1-ol | 0.5% |
| Eucalyptol | 4,7,7-trimethyl-8-oxabicyclo[2.2.2]octane | 14% |
| trans-3-Hexenyl iso-Valerate | hex-3-enyl 3-methylbutanoate | 0.3% |
| dl-Menthyl Acetate | (5-methyl-2-propan-2-ylcyclohexyl) acetate | 2% |
| Weight Percentage Total: | | 96% |

The remaining four percent of Flavor A are unknown or proprietary.

In one embodiment, the flavor composition comprises from 1% to 99% of menthol (e.g., L-Menthol) by weight of flavor composition, alternatively from 10% to 90%, or from 20% to 80%, or from 30% to 70%, or from 40% to 60%, or combinations thereof, of menthol by weight of the flavor composition.

In another embodiment, the flavor composition comprises from 1% to 99% of menthone (e.g., 1-Menthone) by weight of the flavor composition, alternatively from 0.5% to 50%, alternatively from 1% to 40%, alternatively from 2% to 30%, alternatively from 3% to 20%, alternatively from 4% to 15%, alternatively combinations thereof, of menthol by weight of the flavor composition. The amount of flavor composition in an oral care composition is described previously.

Data

Data is provided demonstrating the oral care composition of the present invention having improved freshness. The formulations of inventive and comparative dentifrices compositions are provided in Table 2 below. Flavor Blooming Index ("FBI") methodology is provided (e.g., Tables 3 and 4) and comparative data is provided (Tables 5A, 5B, 6A, 6B) demonstrating the improved FBI of flavor ingredients menthol and menthone. Comparative consumer testing of "coolness" after 40 seconds of brushing the inventive and comparative dentifrice formulation is provided (Table 7). Rheology methodology is described and comparative data is provided (Tables 8A, 8B). Lastly, improved physical stability of the present invention is presented in Table 9.

Formulation Components

Table 2 provides the formulation components of inventive composition of Example 1 (Ex 1) as well as control compositions (Control A, D, E, corresponding to Ex 2, 3, and 4, respectively).

TABLE 2

| Components (wt %) | Ex 1 Inventive | Ex 2 Control A | Ex 3 Control D | Ex 4 Control E |
|---|---|---|---|---|
| Water | 58.87 | 32.08 | 65.47 | 51.57 |
| Sorbitol | 0 | 16.8 | 0 | 0 |
| Sodium Caboxymethyl Cellulose | 0.91 | 1.32 | 0.4 | 0.4 |
| Carrageenan | 1.2 | 0 | 2 | 1.4 |
| Thickening Silica NF (Zeodent™ 165) | 2.62 | 3 | 3 | 0.5 |
| Calcium Carbonate | 32 | 42 | 25 | 42 |
| Sodium Lauryl Sulfate | 1.1 | 2.1 | 2 | 2 |
| TetraSodium Pyrophosphate | 0.6 | 0 | 0 | 0 |
| Flavorant A* | 0.85 | 0.85 | 0.85 | 0.85 |
| Mono Sodium Phosphate | 0.08 | 0.08 | 0 | 0 |
| Tri Sodium Phosphate | 0.42 | 0.42 | 0 | 0 |
| Sodium Saccharine | 0.25 | 0.25 | 0.48 | 0.48 |
| Sodium MonoFluoroPhosphate | 1.1 | 1.1 | 0.8 | 0.8 |
| Total: | 100 | 100 | 100 | 100 |
| pH: | 9.4 | 8.8 | 7.8 | 8.3 |

*Per Table 1 above.

FBI

The "Flavor Blooming Index" or "FBI" is measured as herein described. FBI is defined as the ratio of flavor ingredient intensity over headspace of a diluted oral care composition (e.g., dentifrice slurry) divided by the flavor dosage (e.g., parts per million (ppm)) in the undiluted oral care product (e.g., dentifrice product). FBI reflects the ability of an oral care composition matrix to release a flavor ingredient. In short, the higher the FBI, the higher the release rate is.

Menthol and Menthone are two commonly used flavor ingredients in flavorant compositions. Menthol is usually added for the purpose of a cooling agent, wherein a higher FBI indicates higher coolness flavor effect to the user of the oral care product. Menthone is typically used to deliver a mint character to the flavorant composition. Following method describes how FBI is measured and calculated for menthol and menthone. In turn, the method is also applicable to calculate the FBI for other flavor ingredients.

Flavor intensity over headspace is assessed. A Gas Chromatography-Mass Selective Detector (GC-MSD) equipped with a Multiple Purpose Sampler (MPS) is used to assess the flavor ingredient intensity over the headspace of dentifrice slurry. The method is described for dentifrice, but can be analogized to other oral care compositions. 1 g of dentifrice sample is weighed in a tared 20 mL headspace vial; thereafter 5 glass beads are added in the vial, and then headspace vial is sealed with a septum cap. 3 ml deionized water is injected into the headspace vial via the septum. The sample is vortexed with the glass beads for 40 seconds, 60 seconds, or 120 seconds respectively. The added water and bead mixing represents the action of a user using the oral care composition (e.g., added saliva, tooth brushing etc.). Immediately after vortexing, the vial (containing the dentifrice slurry) is placed onto MPS-GC-MSD sampling tray and assessed. After the MPS-GC-MSD assessment is started, flavor ingredient in the headspace of dentifrice slurry is extracted by SPME (Solid Phase Micro Extraction). The SPME extraction time is set as 15 seconds and the extracts are desorbed in the GC inlet and injected into GC column for separation, followed by MSD detection. All the above operation including SPME extraction, SPME desorption, GC separation, MSD detection can be performed automatically by a MPS-GC-MSD method edited via the manufacturer's instrumental software, taking into the account the chemical structure (ant its properties) of the subject flavor ingredient(s). After the analysis is finished and GC-MSD data is collected, NIST Library is applied to the collected data to identify the interested flavor ingredient(s) and then quantify their target ion response. The target ion response reflects the flavor ingredient's intensity in the headspace of the dentifrice slurry. In order to prevent instrument variation between different labs, a product Control D is used for the purpose of normalization. E.g., the response of Menthol in Control D at 120 seconds should be normalized to 1,000,000 by timing a ratio (1000000/menthol intensity in the current experiment), menthol headspace intensity of other products are adjusted simultaneously using the same ratio. The methodology can be applied to other flavor ingredients.

TABLE 3

MPS-GC-MSD apparatus and methods to measure FBI of oral care compositions (equivalents may be used).
Apparatus & Method

| | |
|---|---|
| MPS-GC-MSD | Gerstel MPS with SPME module |
| | Agilent 7890 Gas Chromatography |
| | Agilent 5975 Mass Selective Detector |
| MPS Condition | SPME sampling is directly from sampling tray with no incubation time. |
| | SPME extraction time is set at 15 seconds; |
| | SPME deporption time is set at 300 seconds; |
| GC Condition | Inlet condition: Inlet temperature is set at 250° C.; using Splitless injection mode; Purge Flow to Split Vent: 50 mL/minute at 2 min; |
| | Oven program: Initial at 60° C., then ramp 6° C./min to 280° C., keep at 280° C. for 5.33 minutes, total run time is 42 minutes; |
| | Column: DB-1, 60M × 0.32 mm I.D. × 1 um film thickness, constant flow at 1.5 ml/min. |
| MSD Condition | Mass mode: Scan |
| | Mass Source temperature: 230° C. |
| | MS Quad temperature: 150° C. |
| Data Analysis Parameters | Flavor Identification: Using NIST library |
| | Target Ion of Menthol: 71 |
| | Target Ion of Menthone: 112 |

The flavor dosage in the undiluted oral care product is assessed (e.g., ppm). Gas Chromatography-Flame Ionization Detector (GC-FID) is used to quantify the amount of the flavor ingredient in the flavor dosage in the dentifrice product (i.e., concentration in the undiluted oral care product). 1 g sample of the dentifrice is vortexed for 30 seconds, or until uniform slurry, with 15 mL of a Dispersing Solution containing ethanol, water, potassium chloride (see Table 4 below) and an Internal Standard (also see Table 4 below) to taken into account any sample to sample variation. 10 mL of hexanes are added to the sample, which is vortexed again, to extract the flavor ingredients into the hexane layer. The hexane layer is allowed to phase separate and a small quantity of it is transferred to a vial containing anhydrous sodium sulfate to remove traces of water from the extract. The anhydrous extract is analyzed on a capillary gas chromatography equipped with a DB-1701 capillary column and a flame ionization detector. With reference to an External Calibration Standard (see Table 4 below), the flavor ingredient(s) in the sample dentifrice is identified and quantified.

TABLE 4

GC-FID apparatus and method to quantify flavor dosage in dentifrice product (equivalents may be used).
Apparatus & Method

| | |
|---|---|
| GC-FID | Agilent 7890 Gas Chromatography equipped with FID detector |
| GC Conditions: | Inlet condition: Inlet temperature is set at 275° C.; using split mode and split ratio is 1:10; Oven program: Initial temperature is set at 40° C., firstly ramp 6° C./min to 72° C.; secondly ramp 1° C./min to 76° C.; thirdly ramp 12° C./min to 120° C., fourthly ramp 2° C./min to 130° C., then ramp 8° C./min to 180° C., finally ramp 30° C./min to 200° C., keep for 6 minutes; Column: DB-1701, 30M × 0.32 mm I.D. × 0.25 um film thickness; FID Detector: 300° C.; $H_2:N_2:O_2$ is set as 30 ml:30 ml:320 ml, respectively. |
| Composition of Dispersion solution: | Dispersion Solution containing cyclohexyl cyclohexanone as Internal Standard is described. First, an Internal Standard Solution of cyclohexyl cyclohexanone is prepared at 4000 ppm in ethanol For 500 ml of Dispersion Solution, it contains 20 ml of said Internal Standard Solution, 80 ml ethanol, 60 ml saturated potassium chloride solution, and 340 ml deionized water. |
| External calibration standard: | A stock external calibration standard containing known level of subject flavor ingredient(s) are firstly prepared in 7:3 ethanol/water (volume to volume) solution. 1 ml of stock calibration standard is prepared following the same extraction procedure as 1 g dentifrice product described in earlier part of this method. |

A summary of the calculation to quantify the flavor ingredient concentration in the undiluted product is provided:

$$\text{Component, ppm} = \frac{\text{Area of component in Sample analysis}}{\text{Area of Istd in Sample analysis}} \times \frac{\text{Area of Istd in standard analysis}}{\text{Area of component in standard analysis}} \times \frac{\text{Weight of component in standard}}{\text{Sample weight}} \times 1000000$$

wherein "Istd" stands for Internal Standard; and wherein Area is obtained from the GC-FID analysis; and wherein Sample weight is the exact weight of the product used in the analysis.

Tables 5A and 5B below detail the FBI of the flavor ingredient Menthone at time points of 40, 60, and 120 seconds after brushing. As illustrated by the data of Table 5B, the FBI of inventive composition Example 1 has an FBI greater than all Controls at all time points. Table 5A provides, for inventive Example 1, as well as Controls A-D, the menthone headspace intensity, menthone dosage in the products, and the FBI of menthone.

TABLE 5A

| | Menthone headspace intensity | | | Menthone dosage |
|---|---|---|---|---|
| Formulas: | @ 40 s | @ 60 s | @ 120 s | in product, ppm |
| Ex 1 | 1517015 | 1468675 | 1481158 | 1026 |
| Control A | 1091742 | 1119905 | 1293716 | 1186 |
| Control D | 929948 | 948149 | 1000000 | 1052 |
| Control E | 974489 | 928678 | 971671 | 1074 |
| Control B | 451199 | 483028 | 533788 | 640 |
| Control C | 283227 | 300777 | 332259 | 987 |

TABLE 5B

| | FBI of Menthone | | |
|---|---|---|---|
| Formulas: | @ 40 s | @ 60 s | @ 120 s |
| Ex 1 | 1479 | 1431 | 1444 |
| Control A | 921 | 944 | 1091 |
| Control D | 884 | 901 | 951 |
| Control E | 907 | 865 | 905 |
| Control B | 705 | 755 | 834 |
| Control C | 287 | 305 | 337 |

Figure 2:
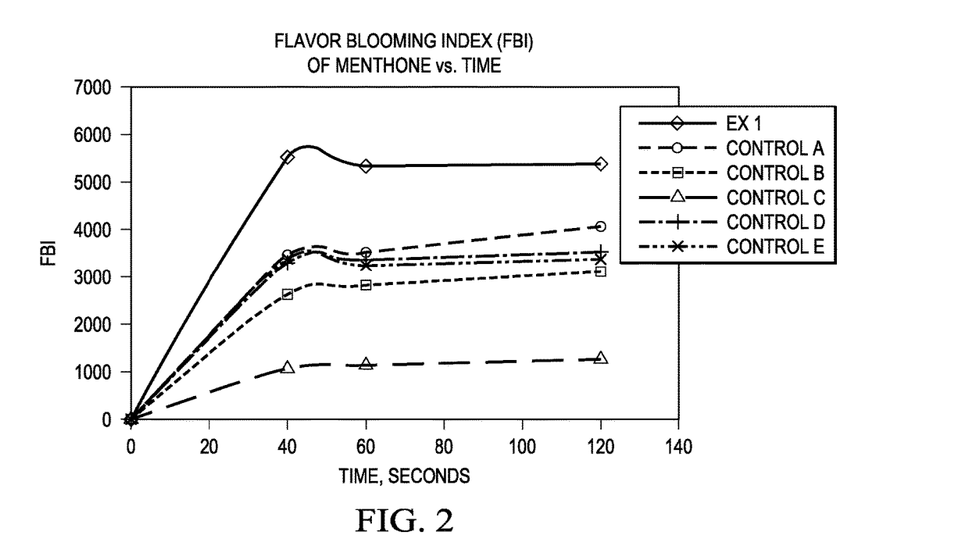
FIG. 2 is a graph of the freshness blooming index of menthone for inventive and control compositions.

FIG. 2 graphs of the data of Tables 5A and 5B illustrating the superior FBI results of the inventive composition of Example 1. In one embodiment, the oral care composition of the present invention comprises a flavor composition, wherein the flavor composition comprises the flavor ingredient menthone, wherein the oral composition has an FBI of menthone greater than 950 at 40 seconds, preferably greater than 1,000, more preferably greater than 1,100, yet more preferably greater than 1,200, yet still more preferably greater than 1,300, alternatively greater than 1,400, alternatively from 1,000 to 2,000, alternatively from 1,100 to 3,000, alternatively combinations thereof. In another embodiment, the oral care composition has an FBI of menthone greater than 950 at 60 seconds, preferably greater than 1,000, more preferably greater than 1,100, yet more preferably greater than 1,200, yet still more preferably greater than 1,300, alternatively greater than 1,400, alternatively from 1,000 to 2,000, alternatively from 1,100 to 3,000, alternatively combinations thereof. In yet another embodiment, the oral care composition has an FBI of menthone greater than 1,100 at 120 seconds, preferably greater than 1,200, more preferably greater than 1,300, alternatively greater than 1,400, alternatively from 1,100 to 2,000, alternatively from 1,200 to 3,000, alternatively combinations thereof.

Tables 6A and 6B below detail the FBI of the flavor ingredient Menthol at time points of 40, 60, and 120 seconds after brushing. As illustrated by the data of Table 6B, the FBI of inventive composition Example 1 has an FBI greater than all Controls at all time points. Table 6A provides, for inventive Example 1, as well as Controls A-D, the menthol headspace intensity, menthol dosage in the products, and the FBI of menthol.

TABLE 6A

| Formulas: | Menthol headspace intensity | | | Menthol dosage in product, ppm |
|---|---|---|---|---|
| | @ 40 s | @ 60 s | @ 120 s | |
| Ex 1 | 1534175 | 1600992 | 1704892 | 3738 |
| Control A | 1033413 | 1151542 | 1365870 | 4221 |
| Control D | 895719 | 945256 | 1000000 | 3923 |
| Control E | 961805 | 938144 | 960387 | 3981 |
| Control B | 1397063 | 1606811 | 1812562 | 5706 |
| Control C | 441332 | 467369 | 557689 | 2742 |

TABLE 6B

| Formulas: | FBI of Menthol | | |
|---|---|---|---|
| | @ 40 s | @ 60 s | @ 120 s |
| Ex 1 | 410 | 428 | 456 |
| Control A | 245 | 273 | 324 |
| Control D | 228 | 241 | 255 |
| Control E | 242 | 236 | 241 |
| Control B | 245 | 282 | 318 |
| Control C | 161 | 170 | 203 |

Figure 3:
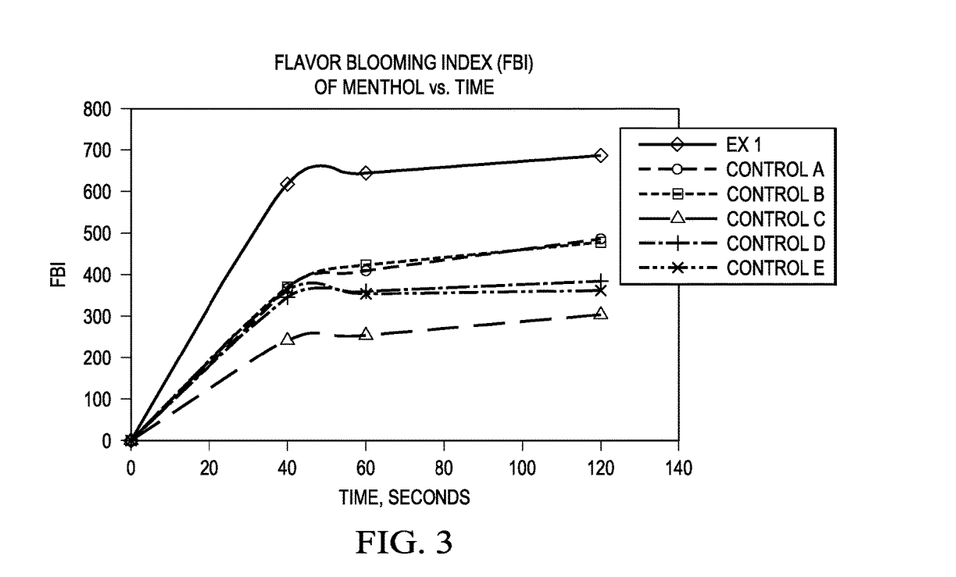
FIG. 3 is a graph of the freshness blooming index of menthol for inventive and control compositions.

FIG. 3 graphs of the data of Tables 6A and 6B illustrating the superior FBI results of the inventive composition of Example 1. In one embodiment, the oral care composition of the present invention comprises a flavor composition, wherein the flavor composition comprises the flavor ingredient Menthol, wherein the oral composition has an FBI of menthol greater than 250 at 40 seconds, preferably greater than 300, more preferably greater than 350, alternatively greater than 400, alternatively from 250 to 1,000, alternatively from 300 to 800, alternatively combinations thereof. In another embodiment, the oral care composition has an FBI of menthol greater than 290 at 60 seconds, preferably greater than 300, more preferably greater than 350, alternatively greater than 375, alternatively greater than 400, alternatively from 300 to 1000, alternatively from 350 to 800, alternatively combinations thereof. In yet another embodiment, the oral care composition has an FBI of menthol 330 at 120 seconds, preferably greater than 350, more preferably greater than 375, yet more preferably greater than 400, alternatively from 340 to 1,000, alternatively from 250 to 800, alternatively combinations thereof.

Consumer Testing of Strength of Coolness

An inventive dentifrice composition has a statistically significant greater coolness effect after 40 seconds than a comparative control composition. A so called Paired Comparison Brush Test Method ("Paired Comparison") is described. The method is essentially a reapplication of China GB 12310-90 (effective since Dec. 1, 1990), and ISO 5495-1983, entitled "Sensory Analysis Methodology-Paired Comparison Test," (1983). Dentifrice compositions of Example 1 (inventive) and Example 2 (control) (see Table 2) are evaluated according to the Paired Comparison test.

18 human panelists are recruited. One half of the panelists started with Example 1 and the other half stared with Example 2. The following testing procedure is used for each panelist. The panelist rinses well with 15 ml CREST® Pro-health Complete mouthwash orally (although other mouthwashes can be used). Thereafter, the panelists eat a plain cracker to remove the taste of rinse. The panelists rinse three times with room temperature tap water to remove the cracker debris. A toothbrush is dosed with 1.2 g of dentifrice. The dosed toothbrush is dipped into tap water, and is gently taped once to remove excess water. The panelists are instructed to use the same brushing habit that the panelist conducts at home for 40 seconds. After brushing, the panelist expectorates the dentifrice from the panelist's mouth and foam into a sink. The panelist rinses with 30 ml room temperature tap water, and record the flavor cooling intensity of the product left in mouth. No further action is taken by the panelists for ten minutes. Thereafter, the panelists eat a plain cracker to wash out their mouth. Ten minutes elapses between finishing the first dentifrice (including eating crackers and washing out their mouth) and beginning to brush with the second dentifrice. Panelists brush with the second dentifrice according to the same protocol described for the first dentifrice's the flavor cooling intensity. Then answer the comparison questions: "Ex 1 is stronger" or "Ex 2 is stronger" or "Ex 1 and Ex 2 are equal strength". The results of the Paired Comparison are provided in Table 7 below:

TABLE 7

| | Coolness @ 40 Seconds | | |
|---|---|---|---|
| | Ex 1 is stronger | Ex 2 is stronger | Ex 1 and 2 equal strength |
| Percent of 18 Panelists: | 62% agree | 16% agree | 22% agree |

The results conclude that a majority of panelist find that inventive Example 1 have a greater coolness flavor than comparative Example 2 (i.e., control). This difference is statistically significant.

Rheology

The unique rheology of the present invention provides the improved freshness. The rheology testing methods of dentifrice macro rheology test and dentifrice yield stress test are described (and ran according to manufacturing instructions). The dentifrice macro rheology profiles are tested on a TA AR2000 rheometer (available from TA Instruments, New Castle, United States) by using Dentifrice Macro Rheology Test procedure. The geometry used is 40 mm steel parallel plate with solvent trap. Dentifrice is placed on the Peltier Plate of AR2000 rheometer and the Gap setting is 1000 micron. Dentifrice Macro Rheology Test consists of stress sweep oscillation, frequency sweep oscillation and steady state flow tests. The key parameter settings are listed: (a)

Stress sweep step: Oscillation Stress (Pa): 0.01-500; (b) Frequency (Hz): 1.0; (c) Frequency sweep step: Frequency (Hz): 0.1-10, and Controlled Oscillation Stress (Pa): 1.5; (d) Steady state flow step 1: Shear rate (1/s): 0.01-100; and (e) Steady state flow step 2: Shear rate (1/s): 100-0.01.

The macro rheology profiles provide the following data points: Average G'; Average G"; 10*K (Pa·s); and (−10000*)n (rate index).

Dynamic oscillation stress sweep is performed to determine the linear viscoelastic region (LVR). LVR is the region where the elastic modulus (G') is independent of applied stress because destruction in the structure of gels occurs at high shear stress. Stress sweep test is designed not to destroy the structure so that the information about intermolecular and interparticle forces in the material can be detected. The three main parameters determined in this test are the storage modulus G', loss modulus G" and Tan δ. Storage modulus G' (also known as an "elastic modulus") is the contribution of elastic (solid-like) behavior to the complex modulus. Loss Modulus G" (also known as "viscous modulus") is the contribution of viscous (liquid-like) behavior to the complex modulus. Complex modulus is the overall resistance to deformation of a material, regardless of whether that deformation is recoverable (elastic) or non-recoverable (viscous). The Average G' is average storage modulus in LVR range of dynamic oscillation stress sweep. The Average G" is average loss modulus in LVR range of dynamic oscillation stress sweep.

Shear flow test is a rheological testing mode to measure the viscosity at different shear rates. Steady state flow test is a flow in which the velocity at every point does not vary with time. The three main parameters in this test are viscosity, shear rate and shear stress. Power Law Model is used to characterize the relationship between viscosity or shear stress and shear rate over the range of shear rates where shear thinning occurs in a Non-Newtonian fluid. It quantifies overall viscosity range and degree of deviation from Newtonian behavior. K and n can be determined by Power Law Model fitting. K is consistency coefficient of Power Law Model and n is rate index of Power Law Model.

Based upon the index, n, the power law model describes three basic types of flow:
n=1 Newtonian behavior
n<1 Shear thinning (or Pseudoplastic)
n>1 Shear thickening $$\text{Shear Stress } (\sigma) = \text{viscosity } (K) * \text{Shear rate } (\gamma)^n$$

The dentifrice Yield Stress test is measured by means of the Brookfield™ HAYR-1 Rheometer with V74 or V75 spindle at room temperature. The rheometer is placed on the Helipath stand and leveled. The selected spindle is attached. The sample container is positioned under the spindle and the temperature probe is inserted along the inner wall of the sample container. The spindle is then immersed into the sample gently until the indicated mark of the spindle is leveled with the surface of the dentifrice sample. The test is run, and the temperature, yield stress (Pa), and percentage torque on the screen is recorded. The test settings are shown: (a) Spindle V75/V74; (b) Zero Speed (rpm) 0.1; (c) Wait Time (sec) 30; (d) Run Speed (rpm) 0.3.

The Yield Stress test provides "10*Yield Stress" defined as the minimum stress to initiate significant flow and a significant drop in viscosity for a shear-thinning composition.

Figure 1:
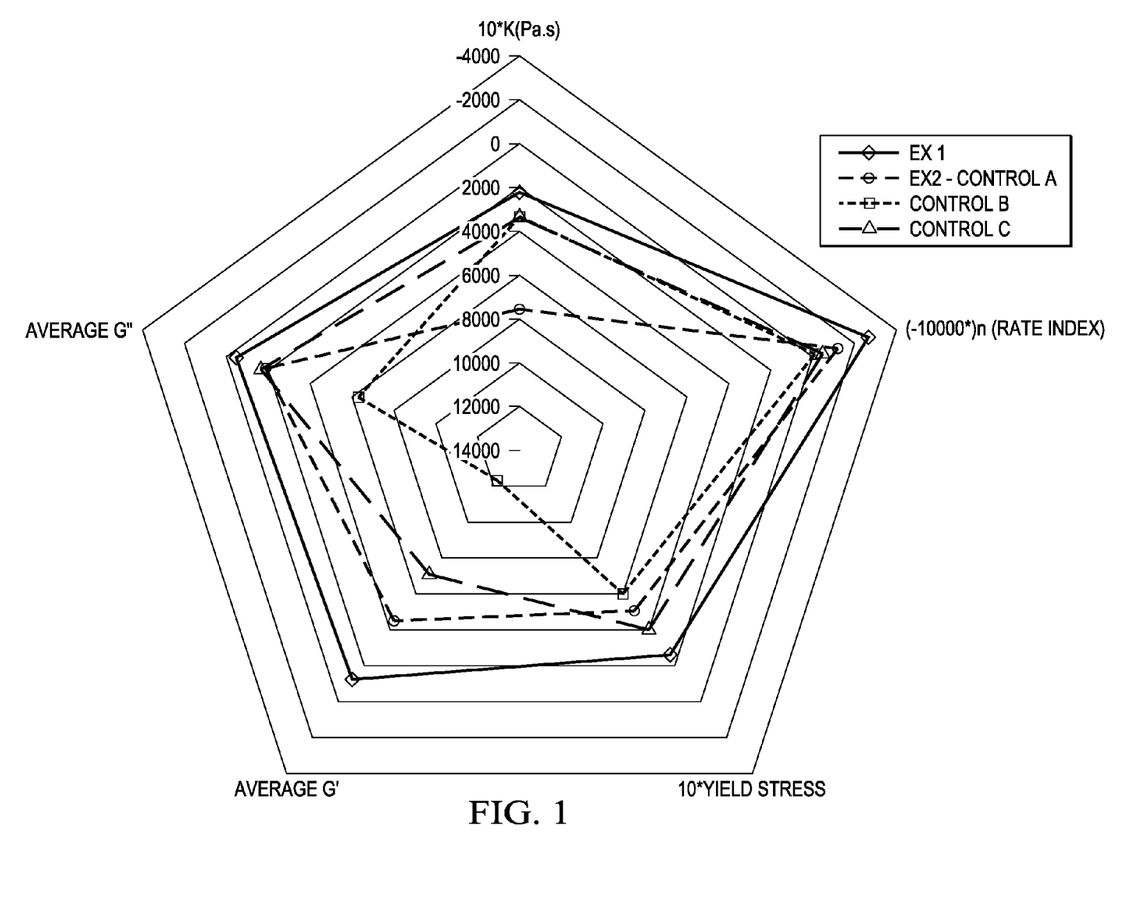
FIG. 1 diagrams rheological parameters for inventive and control compositions.

Based on the rheological methods described, rheological parameters are provided of inventive Example 1 as well as Controls A, B, and C. Table 8 the five rheological parameters of the compositions in question. FIG. 1 maps the results of Table 8 in a graph.

TABLE 8

| | Compositions: | | | |
|---|---|---|---|---|
| Rheological Parameter: | Ex 1 (Inventive) | Ex 2- Control A | Control B COLGATE Brazil[A] | Control C COLGATE India[B] |
| 10*K (Pa · s) | 2260 | 7500 | 3460 | 3160 |
| (−10000*)n (rate index) | −2700 | −1200 | −200 | −600 |
| 10*Yield Stress | 2500 | 5000 | 6000 | 4000 |
| Average G' | 1140 | 4463 | 12300 | 7054 |
| Average G" | 436 | 2057 | 6382 | 1683 |

[A]"COLGATE Brazil-CaCO$_3$" contains a calcium carbonate as well as at least some sorbitol and glycerin. Lot No.: EXP02152055BR12JH
[B]COLGATE Strengthen Teeth (India), Lot No.: 07/13 B13 42.

As demonstrated by the data, inventive composition Example 1 has an Average G' value and Average G" values much lower than the Control compositions. Without wishing to be bound by theory, the rheology profile of the present invention contributes the improved freshness.

Although there are a number of ways of achieving the rheology profile herein described, one way of achieving it is by unique thickening agent system previously described above. Also, another factor that may impact the rheology profile is the presence of a humectant (e.g., glycerol or sorbitol). The inventive compositions may be substantially free or free of a humectant, alternatively of a polyol humectant, alternatively free of sorbitol or glycerol.

In one embodiment, the oral care composition comprises a G' value less than 4,000, preferably less than 3,500, preferably less than 3,000, more preferably less than 2,500, yet more preferably less than 2,000, alternatively less than 1,500, alternatively less than 1,250, alternatively from 100 to 4000, alternatively from 200 to 3,500, alternatively from 300 to 3,000, alternatively from 500 to 2000, alternatively combinations thereof; wherein preferably G' is assessed according to the method as previously described.

In another embodiment, the oral care composition comprises a G" value less than 1,500, preferably less than 1000, more preferably less than 750, yet more preferably less than 500, alternatively from 50 to 1500, alternatively from 100 to 1000, alternatively from 10 to 500, alternatively combinations thereof.

In yet still another embodiment, the oral care composition comprises a rheology profile characterized by at least one parameter of the following parameters, preferably at least any two of the following parameters, alternatively at least any three of the following parameters, alternatively at least any four of the following parameters, alternatively five of the following parameters:

(a) 10*K (Pa·s) value less than 3,000, preferably less than 2,750, preferably less than 2,500, alternatively from 100 to 3,000, alternatively from 1,000 to 2,500, alternatively combinations thereof;

(b) (−10000*)n (rate index) value less than −1500, preferably less than −2,000, more preferably less than −2,500, alternatively from −5000 to −1300, alternatively from −4000 to −1,400; alternatively combinations thereof;

(c) 10*Yield Stress value less than 4000, preferably less than 3,500, more preferably less than 3,000, yet still more preferable less than 2,750, alternatively from 500 to 3,750, alternatively from 100 to 3,500, alternatively combinations thereof;

(d) Average G' value is less than 4,250, preferably less than 4,000, more preferably less than 3,000, yet more preferable less than 2,000, yet still more preferably less than 1,500, alternatively from 100 to 2000, alternatively from 500 to 1,500, alternatively combinations thereof;

(e) Average G" value less than 1,500, preferably less than 1000, more preferably less than 750, yet more preferably less than 500, alternatively from 50 to 1500, alternatively from 100 to 1000, alternatively from 10 to 500, alternatively combinations thereof.

Physical Stability

Another aspect of the invention provides improved physical stability. Improved physical stability is demonstrated as evidenced by demonstrating phase stability (visually to unaided eye) after elevated temperature (30° C.) after 6 weeks. Only inventive Example 1 is phase stable after 6 weeks at 30° C.

TABLE 9

| Relevant Component (wt %) | Ex 1 | Ex 3-Control D | Ex 4-Control E |
|---|---|---|---|
| CaCO₃ | 32 | 25 | 42 |
| TetraSodium Pyrophosphate | 0.6 | 0 | 0 |
| Monosodium Phosphate | 0.08 | 0 | 0 |
| Trisodium Phosphate | 0.42 | 0 | 0 |
| pH: | 9.4 | 7.8 | 8.3 |
| Phase separation after 6 weeks at 30° C. | No | Yes | Yes |

One aspect of the invention provides for no phase separate at 30° C. after 6 weeks with an unaided eye. Alternatively there is no phase separation after 8 weeks, or 10 weeks, or 12 weeks at 30° C.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A dentifrice composition comprising:
   (a) 40% to 70% of water by weight of the composition;
   (b) 25% to 50% of a calcium-containing abrasive by weight of the composition;
   (c) 0.001% to 5% of a flavorant by weight of the composition, and wherein the composition has an Flavor Blooming Index (FBI) of menthol of at least one of the following:
      (i) FBI greater than 250 at 40 seconds;
      (ii) FBI greater than 290 at 60 seconds; and
      (iii) FBI greater than 330 at 120 seconds;
   (d) 0.01% to 1.35% of tetrasodium pyrophosphate by weight of the composition; and
   (e) from 0.1% to 1.3% of a carrageenan by weight of the composition;
   (f) from 0.5% to 1.8% of a carboxymethyl cellulose by weight of the composition;
   (g) 0.5% to 5% of a thickening silica by weight of the composition;
   (h) 0.1% to 12% of sodium lauryl sulfate surfactant by weight of the composition; and
   (i) pH from 8.5 to 12
   (j) a rheology profile characterized by at least one of the following parameters:
      (i) 10*K (Pa·s) value from 100 to 3,000;
      (ii) (−10000*)n (rate index) value from −5000 to −1300;
      (iii) 10*Yield Stress value from 100 to 3,500;
      (iv) Average G' value from 100 to 2000;
      (v) Average G" value 100 to 1000;
   wherein the composition comprises from 0% to 5% of a humectant by weight of the composition;
   wherein the humectant is selected from the group consisting of glycerin, sorbitol, and combinations thereof.

2. The composition of claim 1, wherein the rheology profile is characterized by Average G' value from 10 to 1,500.

3. The composition of claim 1, wherein the rheology profile is characterized by Average G" value from 10 to 500.

4. The composition of claim 1, having visibly no observable phase separation after 6 weeks at 30° C. with an unaided eye.

5. The composition of claim 1, wherein the flavorant composition comprises a menthol; and wherein the composition has an Flavor Blooming Index (FBI) of menthol of at least two of the following:
   (i) FBI from 300 to 800 at 40 seconds;
   (ii) FBI from 300 to 1000, at 60 seconds; and
   (iii) FBI greater than 330 at 120 seconds.

6. The composition of claim 1, wherein the flavorant composition comprises a menthol; and wherein the composition has a Flavor Blooming Index (FBI) of menthol of at least three of the following:
   (i) FBI greater than 950 at 40 seconds;
   (ii) FBI greater than 950 at 60 seconds; and
   (iii) FBI greater than 1,100 at 120 seconds.

7. The composition of claim 1, wherein the composition has a rheology profile characterized by at least one parameter of the following parameters:
   (i) 10*K (Pa·s) value from 100 to 3,000;
   (ii) (−10000*)n (rate index) value from −5000 to −1300;
   (iii) 10*Yield Stress value from 500 to 3,750;
   (iv) Average G' value from 500 to 1,500; and
   (v) Average G" value from 100 to 1000.

* * * * *